(12) United States Patent
Zhou

(10) Patent No.: US 8,559,004 B1
(45) Date of Patent: Oct. 15, 2013

(54) METHOD AND APPRATUS FOR EMISSION SPECTROSCOPY UTILIZING A FLAT PLATE FOR SAMPLE HOLDING AND EXCITATION

(76) Inventor: Zhou Zhou, Shrewsbury, MA (US)

( * ) Notice: Subject to any disclaimer, the term of this patent is extended or adjusted under 35 U.S.C. 154(b) by 66 days.

(21) Appl. No.: 13/204,678

(22) Filed: Aug. 6, 2011

Related U.S. Application Data

(60) Provisional application No. 61/469,056, filed on Mar. 29, 2011.

(51) Int. Cl.
*G01J 3/30* (2006.01)

(52) U.S. Cl.
USPC ....................................... 356/313

(58) Field of Classification Search
USPC ....................................... 356/313
See application file for complete search history.

(56) References Cited

U.S. PATENT DOCUMENTS

| | | | |
|---|---|---|---|
| 2,920,201 A * | 1/1960 | Annis et al. ................. 356/313 |
| 3,736,059 A * | 5/1973 | Schuhknecht et al. ........ 356/313 |
| 5,408,306 A | 4/1995 | Anderson |
| 5,982,847 A | 11/1999 | Nelson |
| 6,452,179 B1 * | 9/2002 | Coates et al. ............ 250/339.09 |
| 6,455,850 B1 | 9/2002 | Coates |

* cited by examiner

*Primary Examiner* — Tarifur Chowdhury
*Assistant Examiner* — Abdullahi Nur

(57) ABSTRACT

An apparatus for multi-elemental analysis comprises an excitation site (1, 31) having an extended flat surface area for holding sample to be excited, and being adaptive to plural physical forms of sample and to retention of large wear metal particles which, in turn, appear as an uneven spatial distribution of elements on the surface. A scan mechanism (12-13, 32) is associated with the excitation site, a spectrometer, and an excitation source for evaluating the emission from each point in a defined region on the surface. A method of using the excitation site for retaining and analyzing inhomogeneous ingredients in a sample is provided. The apparatus further includes a heating mechanism (18, 34) for heating the sample on the surface.

9 Claims, 6 Drawing Sheets

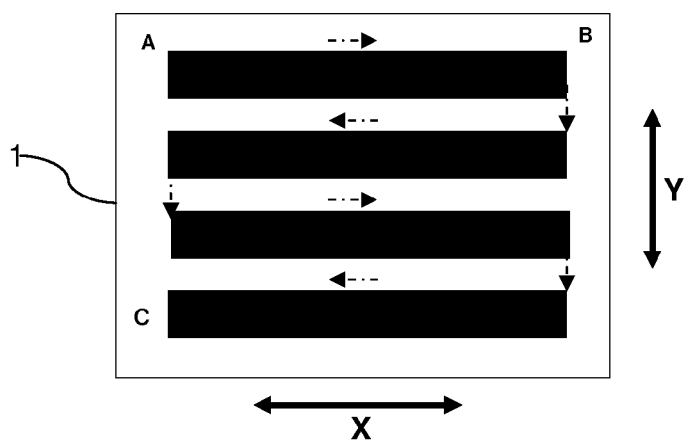
FIG. 3
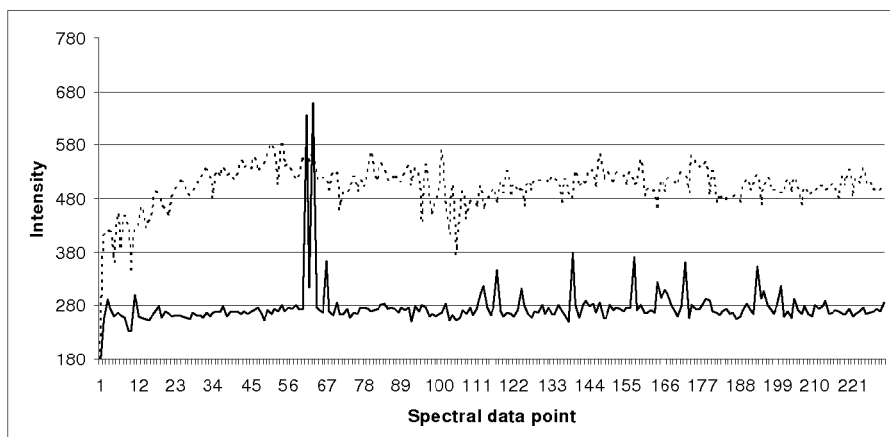
FIG. 4-1
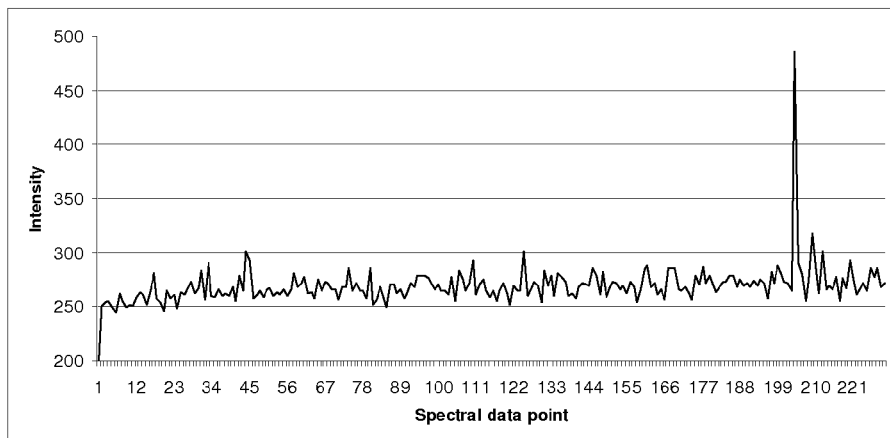
FIG. 4-2
FIG. 4

METHOD AND APPRATUS FOR EMISSION SPECTROSCOPY UTILIZING A FLAT PLATE FOR SAMPLE HOLDING AND EXCITATION

CROSS-REFERENCE TO RELATED APPLICATIONS

This application claims the benefit of provisional patent application Ser. No. 61/469,056 filed 2011 Mar. 29 by the present inventor.

TECHNICAL FIELD

The present invention relates to application of emission spectroscopy from atomic excitation for analyzing samples wherein the presence of chemical elements may be non-homogeneous. In particular, the present invention relates to an emission spectroscopy method and apparatus for wear metal analysis.

BACKGROUND

The following is a tabulation of some prior art that presently appears relevant:

| U.S. Pat. Nos. | | | |
|---|---|---|---|
| U.S. Pat. Nos. | Kind Code | Issue Date | Patentee |
| 6,455,850 | B1 | 2002-9-24 | Coates |
| 6,452,179 | B1 | 2002-9-17 | Coates |
| 5,408,306 | | 1995-4-18 | Anderson |

Emission spectroscopy is based on re-emission of the energy absorbed by an atom from an excitation process. Once an atom of an element is excited by a form of energy, its atomic structure is distorted to an unstable state, just as a compression-coil spring is compressed by force. The unstable state cannot be held, just as the compressed spring tends to recover to its relaxed state. When the spring bounces back to its relaxed state, mechanical energy stored by the spring is released. So do the excited atoms, but for atoms, the energy stored in their atomic structure is released by emitting light. Because each element has a unique atomic structure, its emission spectrum is uniquely related to its atomic structure, that is, it emits light only at certain wavelengths, called characteristic wavelengths of the element. For example, one of the characteristic wavelengths of copper is 324.75 nm (nanometer). If a peak of the light emitted by a sample appears at 324.75 nm, it is a positive identification of the existence of copper in the sample. On the other hand, the concentration of an element in a sample is proportional to the intensity (peak height) of the light emitted at the characteristic wavelengths. Thus Emission spectroscopy provides a means for knowing the existence and quantity of the element in the sample. The advantage of emission spectroscopy is that plural elements simultaneously emit light upon excitation, and thus the existence and concentration of the plural elements in a sample can be determined by a single excitation process.

A plurality of forms of energy can be used to excite atoms. One form of the energy is heat or high temperature plasma. Electric spark can provide the heat. Spark can be generated by applying a high voltage to a spark gap consisting of two electrodes. Sample is presented to the spark gap for excitation, which, in turn, produces emission spectra of elements in the sample. Laser is another approach to provide the heat. Once a pulsed laser beam is directed at a sample, a spot of the sample is heated by laser power to give emission spectra, which is called Laser Induced Breakdown Spectroscopy (LIBS). Another form of the energy is X-ray. Once an X-ray beam strikes a sample, the atoms in the sample are excited to produce an emission spectrum, called X-Ray Fluorescence (XRF) spectrum.

A typical apparatus of emission spectroscopy comprises an excitation site, where excitation energy is exposed to a sample, an excitation source for generating the energy, and a spectrometer for collecting the light emitted from the excitation site. The spectrometer is an apparatus that sorts light by wavelengths and measure the intensity of the light at any given characteristic wavelengths. Thus the information required for knowing the existence and quantity of any elements in the sample is both provided by the spectrometer.

Oil analysis provides information of wear occurred inside a compartment of mechanical equipment. If mechanical equipment is serviced by lubricant oil, the elements worn off from a moving part, such as a gear, may enter the oil in the form of metal particles. By analyzing the elemental types of the wear metals and their quantities, the internal conditions of the equipment and the degree of wear can be learned without having to disassemble it for a visual inspection. Thus oil analysis tells what the wear metals are, e.g., iron, aluminum, copper, and so on, and how much they are. For oil analysis, emission spectroscopy is a preferred tool because of its capacity of analyzing multi-elements in used oil by a single excitation.

Non-homogeneity is a problem for used-oil samples containing wear metals. Wear metals are not entirely dissolved in oil but exist in the form of particles with various sizes. These particles are suspended in the sample. But the suspension is not even. For example, large particles can quickly settle down to the bottom of a sample bottle while fine particles may stay everywhere in the bottle. As a result, at the bottom part of the bottle, the concentration of a wear metal is higher than that at the upper part. On the other hand, the existence of larges particles often reveals the events of severe wear or damage, while that of fine particles often results from chronically normal wear. Because the existence of large particles of wear metals may be evaluated as a precursor of a potential catastrophic failure for mechanical equipment, capturing and detecting the large particles is always an object of method development for oil analysis.

When reviewing the related art, two questions are in consideration. Firstly, whether the large particles can be captured and presented to the excitation site of an apparatus for producing emission? Secondarily, if the large particles can be captured and presented to the excitation site, whether their existence can be recognized? To understand the second question, consider this scenario, if a sample does not contain many fine particles but just a few of large particles, the overall concentration of corresponding wear metals is still low, not high enough to trigger a warning, because the strong emission signal from the large particles is averaged by overall weak emission signal. Thus the existence of large particles may not be recognized.

The most conventional method for exciting an oil sample is spark. However, because the electrode forming a spark gap has a limited cross-sectional area for holding the sample, continuously flowing of the sample to the tip of the electrode has to be maintained.

One approach to transport the oil sample to the spark gap is to configure the lower electrode of the spark gap into a wheel, called Rotating Disk Electrode (RDE), as described by U.S. Pat. No. 5,408,306 issued to Anderson on Apr. 18, 1995. The rotating disk is mounted vertically against a small sample container, with its lower part submerging into the sample fluid. The fluid contacts the disk and films on the disk circumference. The top part of the click forms the spark gap with an upper electrode. The vertical rotation of the disk brings the fluid-filmed circumference up to be exposed to the upper electrode of the spark gap. Continuous rotation is maintained during excitation and thus the fluid from the sample container is continuously fed to the spark gap. This approach is called conventional RDE analysis.

Another approach to transport the oil sample is to force it to flow into a spark gap, as disclosed by U.S. Pat. No. 6,455,850 B1 issued to Coates on Sep. 24, 2002. In this mechanism, the lower electrode of the spark gap is configured as an outlet of a fluid supplying conduit. The inlet of the fluid conduit is inserted into a sample bottle. A pump is used to mobilize the fluid through the fluid conduit and forces the fluid to flow through a through-bore portion of the lower electrode. Thus the fluid can continuously enter the spark gap.

The common feature of the two approaches is to provide a continuous flow of fluid for transporting a sample to a spark gap. The approaches solve the problem of sample supply for the spark gap, but cannot capture particles with the size greater than 0.03 mm and present them to the spark gap. The reason is simple: if a particle cannot be suspended by a fluid, it cannot flow with the fluid, such as river water cannot carry or move large stones to down stream because of the gravity of the stone.

For capturing large particles of wear metals, another approach with the RDE is also disclosed by the same U.S. Pat. No. 5,408,306. In summary, this approach captures the large particles from a sample by using a filter, and then analyzes the captured large particles independently. Then the same sample is analyzed by conventional RDE analysis, in which the large particles are absent. This approach provides a way to identify the existence of large particles, but involves a multiple step procedure and additional apparatus for filtering the sample.

Though there are always some analytical methods that are able to identify the existence of large particles, these methods are laboratory procedures requiring multi-step sample pretreatment, such as filtering, diluting, thermo-decomposition of oil samples, acidic-dissolving, solvent-washing, and so on. Apparently, these methods are disadvantaged for delayed report, resource-and-time consuming, and skill-demanding. It would be desirable to provide an apparatus that can conduct immediate analysis of a used oil sample while without missing large particles if there are any. Especially, it would be desirable to generate reports of the analysis on-site.

In addition, compared to emission spectroscopic apparatus based on laser or X-ray, a spark apparatus costs the least, and provides the most conventional and successful method for oil analysis. However, the requirement of continuous flow of sample fluid limits its application only to oil. Other chemicals servicing mechanical equipment, such as grease and coolant, possess equal importance of analysis of wear metals and have the same inhomogeneous issues caused by mixed or suspended particles. To date, even though one has invested a spark apparatus for on-site oil analysis, one still has to ship grease and coolant samples to a remote laboratory for analysis. It would be desirable to expand the usage of a spark apparatus to a plurality of forms of samples, such as grease, coolant, vessel fuel, and so on, in addition to oil.

It is understood that warming a viscous lubricant sample improves its excitation. It would be desirable to provide a means to heat-bath the sample before or during the excitation leading to emission spectroscopy.

Insofar as I am aware, the emission spectroscopy based on XRF and LIBS cannot provide a method to distinguish large particles from small ones without employing some kinds of sample-pretreatments, such as filtering and solvent-washing. In conclusion, there is a need to provide an improved method and apparatus to address the problems as set forth above, and for all types of atomic excitation approaches, including, but not limited to, spark, X-ray, and laser-induced-breakdown.

SUMMARY

In accordance with one embodiment, there is a provided method of performing emission spectroscopy with a flat sample plate possessing an extended surface area. A sample is spread onto the entire surface of the sample plate, which is moved by an XY mobile system. Excitation is carried out point by point on the surface, and emission spectra are acquired point by point, too.

In one embodiment, conventional spark is used as the means of excitation, and thus the sample plate also serves as the lower electrode of a spark gap.

In other embodiments, laser or X-ray generator provides excitation energy.

In another embodiment, the mobile system comprises a rotary table.

According to one aspect of the present invention, there is a provided method for capturing large wear metal particles from a sample for emission spectroscopic analysis.

According to another aspect of the present invention, there is a provided method for distinguishing the captured large particles from small particle background without using a filter to physically separate them.

According to another aspect of the present invention, there is no limitation to the physical forms of samples to be excited.

According to another aspect of the present invention, there is a provided method for heat-bathing the excitation site before and/or during excitation.

ADVANTAGES

Accordingly several advantages of one or more aspects are as follows: to provide a simple and low cost emission spectroscopic apparatus and method that is able to capture and identify large wear metal particles in a sample without actually separating them with a filter, that allows a single apparatus to analyze different forms of samples, including, but not limited to, oil, grease, coolant, and vessel fuel, that allows sample to be warmed during excitation, and that allows an immediate on-site analysis to be operated by non-skilled workers. Other advantages of one or more aspects will be apparent from a consideration of the drawings and ensuing description.

BRIEF DESCRIPTION OF THE DRAWINGS

FIG. 3 is a plane view of an XY scan route for the first embodiment.

FIG. 4 is intensity profiles of example elements at some characteristic wavelengths.

DETAILED DESCRIPTION

Figure 1:
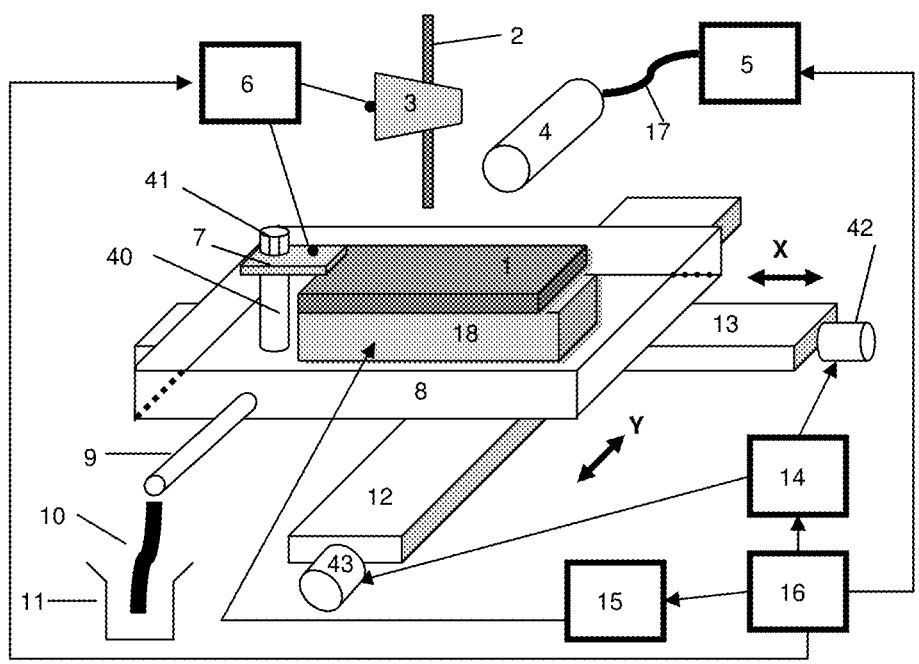
FIG. 1 is a schematic representation of the first embodiment.

FIG. 1 describes the first embodiment. The excitation source is a conventional sparker 6, or a controlled high voltage power supply.

The excitation site is a spark gap consisting of two electrodes. The upper electrode 2 is an electric conductive rod and clamped by a metal mechanism 3, and is connected to one end of the sparker 6 via the mechanism 3. The lower electrode 1 is an electric conductive flat plate, and is connected to another end of the sparker 6. The lower electrode 1 possesses an extended surface area for holding the sample to be excited. The upper electrode 2 is mounted perpendicular to the surface of the lower electrode 1 and points to a point of the surface. Thus the spark gap is configured by a point of the surface of the lower electrode 1 and the lower tip of the upper electrode 2. The surface area of the lower electrode 1 is larger than the cross-sectional area of the upper electrode 2, so that the latter is considered a point segmenting the surface. I presently contemplate for this embodiment that the lower electrode 1 has a size of 44.5 mm by 40.6 mm by 3.2 mm, and is flat without rim. However, it can have different sizes and may possess a shallow rim for holding fluid. In my contemplation, both the lower electrode 1 and the upper electrode 2 may be made of carbon, which is inexpensive and has a porous surface. However, other materials can be used as long as the materials do not contain the chemical elements to be analyzed. For the built embodiment, both electrodes 1 and 2 were obtained from JiXing ShengAn Company, Xihongmen Xing Sanyu Dong, Daxing District, Beijing, China.

In the built embodiment, the lower electrode 1 is horizontally held in the inside of a fluid pan 8 by a metal connector 7, which also provides an electric connection to the return wire of the sparker 6. The connector 7 is mounted on its base 40 and fastened by a screw 41. However, other mechanisms can be used to hold the electrode 1, such as clamps or molded slots. In the built embodiment, the electrode 1 is held only at one side, but for better effect, it can be held at two or more sides. The connector base 40 is mounted on the fluid pan 8.

Between the electrode 1 and the fluid pan 8, a heater-thermistor assembly 18 is sandwiched. The heater-thermistor assembly 18 provides heat energy to the lower electrode 1. I presently contemplate for this embodiment that a conventional heating pad is used as a heat generator. However, a TE cooler or microwave source also can provide the heat energy. Another probable way is to exert electric current to the two opposite ends of the lower electrode 1, with which the lower electrode 1 itself generates the heat energy because of its internal electric resistance. A temperature controller 15 provides electric energy to the heater 18 and reads back the temperature to a computer 16. The heating power of temperature controller 15 is commanded by the computer 16. Thus the heating temperature of the lower electrode 1 can be maintained at a preset value. In the built embodiment, the heating pad is powered by a 24V DC power supply and provides adjustable temperature up to 93° C.

The fluid pan 8 comprises a drainage 9 to receive extra fluid flowing out of the lower electrode 1. The drainage 9 is connected by a soft tube 10 which provides a fluid conduit for discharging the extra fluid to a waste container 11. The reason to use a soft tube 10 is that the fluid pan 8 is movable relative to the position of the waste container 11. In my contemplation, the fluid pan 8 is made with plastic material in order to provide electric insulation for the lower electrode 1. However, if such insulation is not required, other materials can be used.

A conventional X-Y table is a two axis positioning mechanism driven by two motors. The X-Y table provides the lower electrode 1 with a precision-controlled automated movement in X and Y directions against the upper electrode 2. Two dimensional motion can increase the length of trip for more coverage of sample. However, one dimensional motion is also fine if the lower electrode 1 is made with enough length, for which the X-Y table can be reduced to a linear moving stage. The fluid pan 8 is mounted on the carriage (not shown) of an X-table and can move on the surface of the X-guide way 13, driven by an X-motor 42. The X-guide way is mounted on the carriage (not shown) of a Y-table and can move on the surface of the Y-guide way 12, driven by a Y-motor 43. Thus the lower electrode 1 can move freely in x and y axes respectively and a two dimensional scan mechanism is thus provided. The X-motors 42 and the Y-motor 43 are controlled by a motion controller 14, which is commanded by the computer 16. The driving mechanism, position control and its electronics for the X-Y table are well known to those who practice in this art and are not deliberated in this teaching.

A spectrometer assembly comprises a fiber optical collimator/focuser 4 and a conventional optical CCD spectrometer 5, in which the former collects the light emitted from spark plasma and transfers the light to the latter via a fiber optical cable 17. The collimator 4 is commercially available and can be supplied by many vendors, for example, OLE Land Inc, in LaSalle, Quebec, Canada. Similar to the upper electrode 2, the collimator 4 has a fixed position in the X-Y plane with its view is always aimed at the lower tip of the upper electrode 2, where the excitation occurs. The wavelength range of the spectrometer 5 is from 220 to 360 nm.

Figure 2:
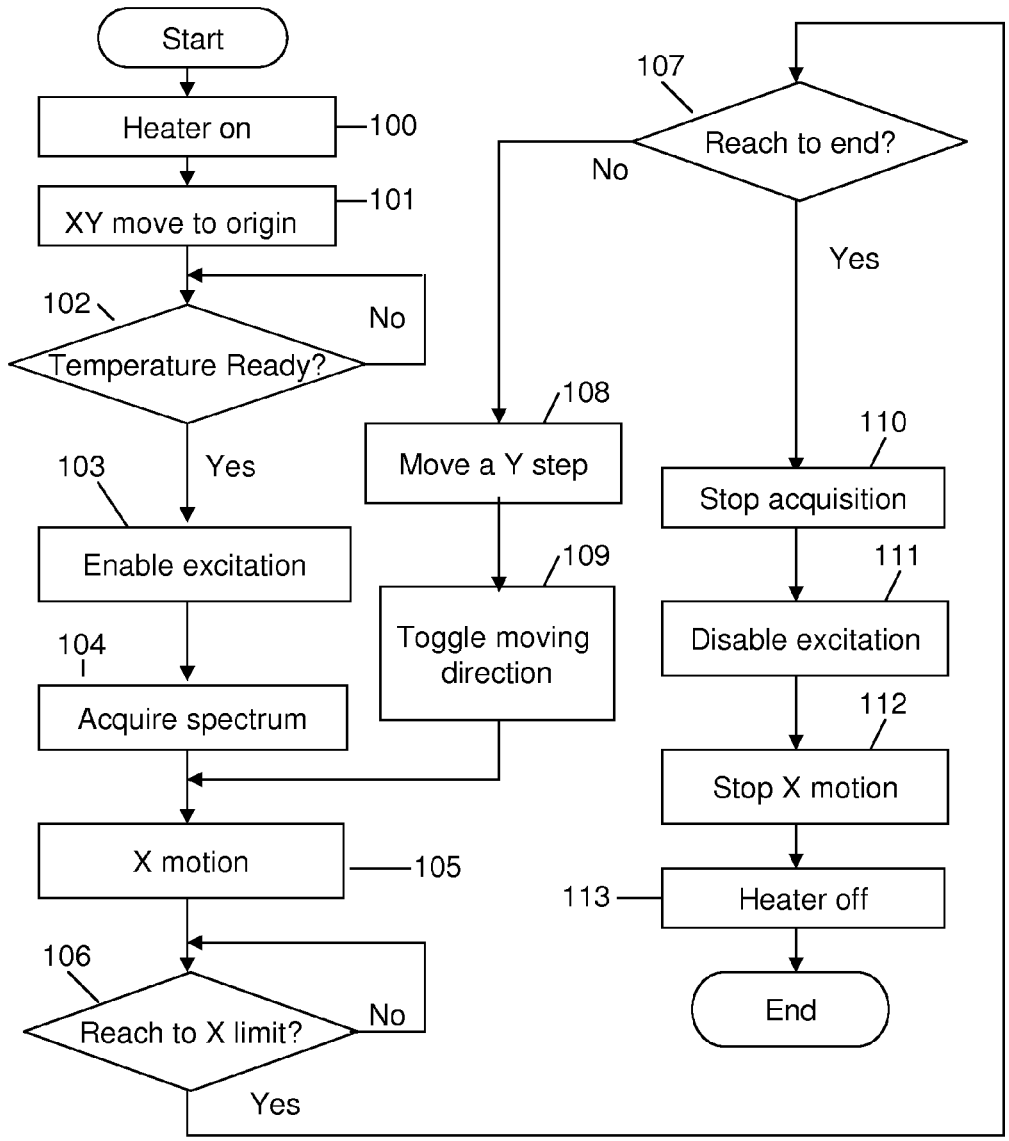
FIG. 2 is a simplified flowchart diagram of controls by a computer.

The computer 16 controls each module, including but not limited to, the sparker 6, the motion controller 14, the spectrometer 5, and the heater-thermistor assembly 18. FIG. 2 shows essential steps for the computer 16 to execute the motion for a scan, excitation, the acquisition of spectra, as well as the thermal control for the sample.

To operate, one first places a clean lower electrode 1 onto its position, and fixes it with the connector 7 and the screw 41. If the sample is fluid, such as oil or coolant, it can be directly down-poured onto the surface of lower electrode 1 so that the entire area of the lower electrode 1 is covered by the fluid. Once the fluid reaches the surface of the lower electrode 1, the flow direction of the fluid is changed from a down flow to a laminar flow, and thus the flowing of large particles loses momentum and tends to stay on the surface. Since the fluid cannot accumulate on the flat surface of the lower electrode 1, extra fluid escapes out of the surface and flows down to fluid pan 8 and finally the waste container 11 via the drainage 9 and the soft tube 10, leaving a film of the fluid on the entire surface of the electrode 1. Because fine particles are fully mixed with the fluid, the film of oil contains fine particles. This way to introduce a sample to the excitation site posts no limitation to the sizes of particles because the particles with all sizes have the same chance to reach to the surface of the lower electrode 1. Thus both large and fine particles are captured.

During excitation, spark plasma is only localized directly under the tip of the upper electrode 2, and thus solely a portion (a point of a surface) of the sample film on the surface of the lower electrode 1 is excited. The relative motion between the lower electrode 1 and the upper electrode 2 supplies unexcited sample film to the spark gap, which is equivalent to a continuous flow of fluid, as realized by the means of a pump or a rotating disk. The XY movement provides the lower electrode 1 being scanned by the upper electrode 2, that is, by the spark gap, that is, by the excitation source.

If the sample is lubricant grease or non-flowable chemicals, it can be manually spread onto the entire surface of the lower electrode 1, and then be continuously transported to the spark gap in the same way as for a fluid sample. There is still no limitation to the size of particles mixed in the grease sample.

Furthermore, because the introduction of a sample to the spark gap in this embodiment does not post any restrictions to the forms of the sample, coolant, which also possesses the importance of analysis of wear metals, can be also analyzed by conventional spark method.

Accordingly, advantages immediately appear: capturing large particles, adaptive to any forms of samples, including non-flowable chemicals, such as grease, varnish or sewer, as well as coolant, immediate analysis without sample-pretreatment, and simple operation.

FIG. 3 is an illustration of a scan route for the lower electrode 1. To start a scan, the computer 16 is programmed to move the lower electrode 1 to point A in FIG. 3, where is the start position for the upper electrode 2 to form a spark gap with the lower electrode 1. Once the temperature reaches to a preset value, the sparker 6 starts to excite the sample around point A. Meanwhile, the X motor 42 begins to move the lower electrode 1 at a constant speed in X direction, and the spectrometer 5 starts to acquire spectra through the collimator 4. Once the upper electrode 2 arrives point B, the X motor 42 stops and the Y motor 43 moves the lower electrode 1 one step forward in Y direction. And then the lower electrode 1 is moved left in X direction for a new row of the scan route. The computer 16 repeatedly executes operation until point C in FIG. 3 is reached. And the spectrum acquired for each point is stored in a sequence corresponding to the scan route.

The spatial resolution or pixel size of the scan is determined by multiplying the linear speed of the electrode 1 by the acquisition time of the spectrometer 5, and then plus the diameter of the upper electrode 2. For example, if the linear speed is 1 mm per second, the acquisition time 0.5 second, and the diameter 6 mm, then the pixel size is 6.5 mm in length by 6 mm in width, which is the area of a point a spectral data point represents. Thus the segmentation of the surface is defined by the size of the pixel or the point.

In the built embodiment, both X and Y linear speeds of the lower electrode 1 are set at 0.9 mm per second, and the Y step is 6.2 mm. All the motion parameters can be adjusted by the computer 16 for best experimental results.

FIG. 4 plots the intensities of acquired spectral data points at different characteristic wavelengths, in which each intensity value represents the light emitted from a pixel or a point on the surface of the lower electrode 1 by an element of interest.

By averaging the intensities from all points, an averaged or overall concentration of the element in the sample, representing both fine and large particles, is obtained. However, the spirit is to collect, register, and evaluate the emission from a single point on the scanned surface of the lower electrode 1.

If a sample is not homogeneous, the distribution of elements spreading on the surface is not even, that is, at some points, the concentration of an element would be higher than that at others. Correspondingly, the intensities of the emitted light can be spatially discriminated. If there are large particles at some points, the intensity of the light emitted from those points would elevate. In an experiment, a few large metal particles were mixed with a used oil sample, in which some particle size is bigger than 0.5 mm. The data from this sample is shown by the solid-line trace in FIG. 4-1. Strong peaks from the emission of large particles can be clearly observed, while the low terrain, the intensity level at about 280, is the emission from fine particles of the metal in the used oil. An intensity reading deems to be significant and to indicate the presence of large particles when it is sufficiently greater than the average background to stand out from the background. With this method, the existence of a few large particles can be distinguished disregarding the concentration of fine particles, which eliminates filtering and other multi-step-pretreatment for distinguishing large particles.

In contrast, if the distribution of an element is homogeneous in the sample, the corresponding intensity should be noise-like. The dash-line trace in FIG. 4-1 is obtained from an element existing in the same sample in a molecular form, which means the element can homogenously stay in the sample. It can be seen that though there are big ripples, there are no peaks significantly standing out from its ripple background.

For high value equipment, such as airplanes, oil is changed more frequently than necessary. Because of the shortened service period, fine particles may not accumulate in used oil. However, once mechanical problem occurs, a few of metal debris (large particles) may enter oil. These large particles may not be detectable because the used oil is much like fresh oil, giving an overall low emission that averages out their emission. To simulate this case, a few of metal debris were placed on the lower electrode 1 with a fresh oil sample. The result is displayed in FIG. 4-2. A strong emission from the metal debris at data point 200, approximately, can be identified. The strong emission peak can warrant a warning for a likely catastrophic failure, although the overall concentration of the wear metal is low.

Viscous sample, such as grease and heavy-duty gear oil, absorbs excitation energy. Heat energy can soften the sample and increase the penetration of excitation energy for improved sensitivity and matrix effect. For coolant sample, the heat energy can remove water from the sample and may reduce the interference of water vapor to the analysis. The extended surface area of the lower electrode 1 provides an increased flux for the heat energy to reach to the surfaced sample. And also the sample can be heat-bathed during excitation, which is necessary when the apparatus is working in cold environment like in-field or on-site.

Figure 5:
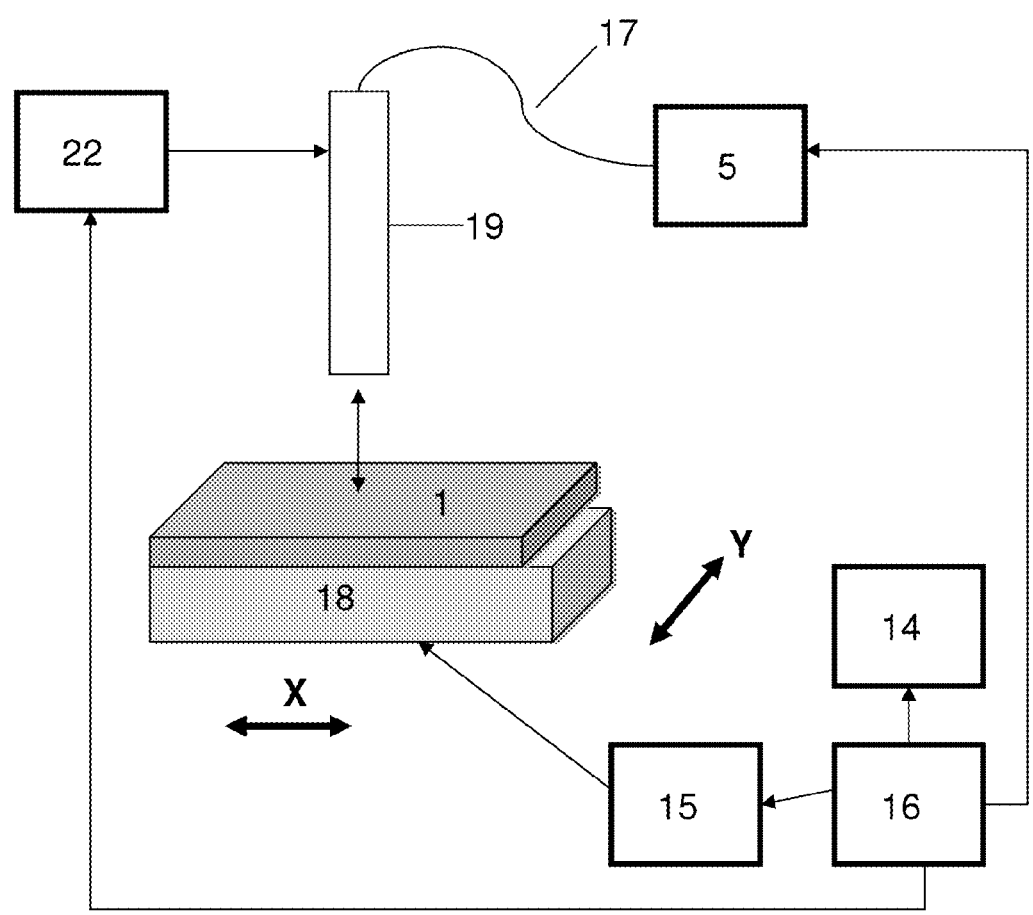
FIG. 5 is a simplified schematic representation of an embodiment comprising LIBS.
Figure 6:
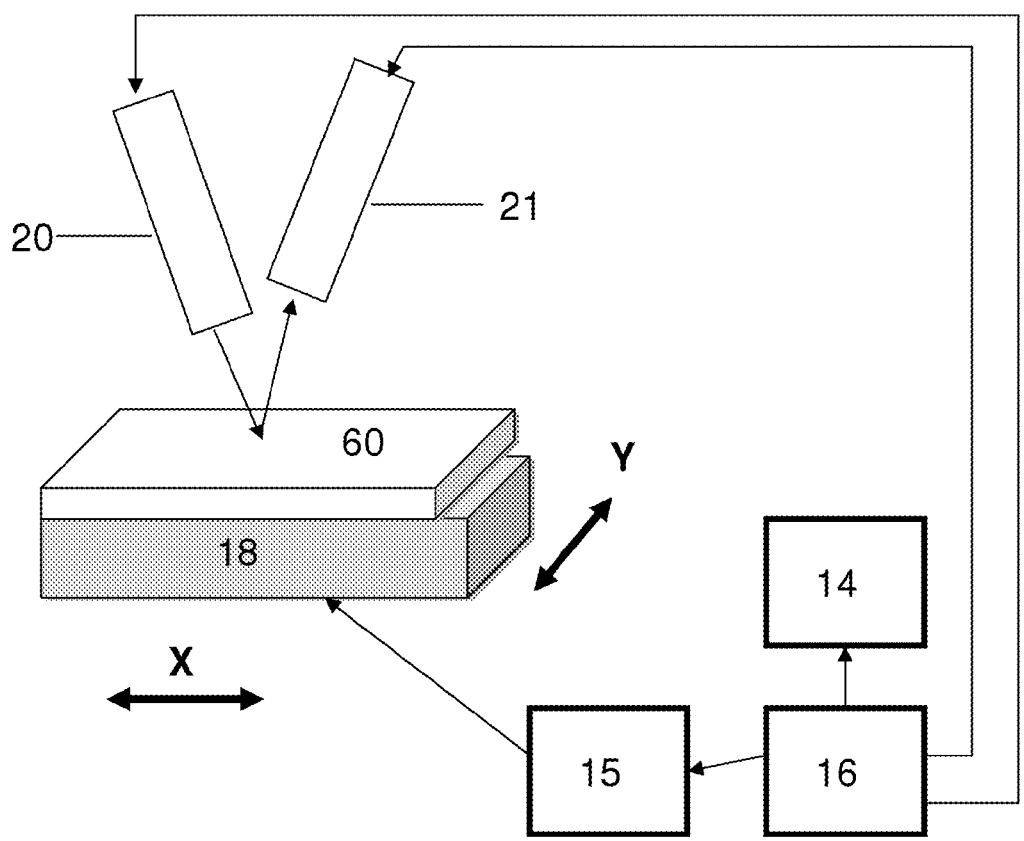
FIG. 6 is a simplified schematic representation of an embodiment comprising XRF.
Figure 7:
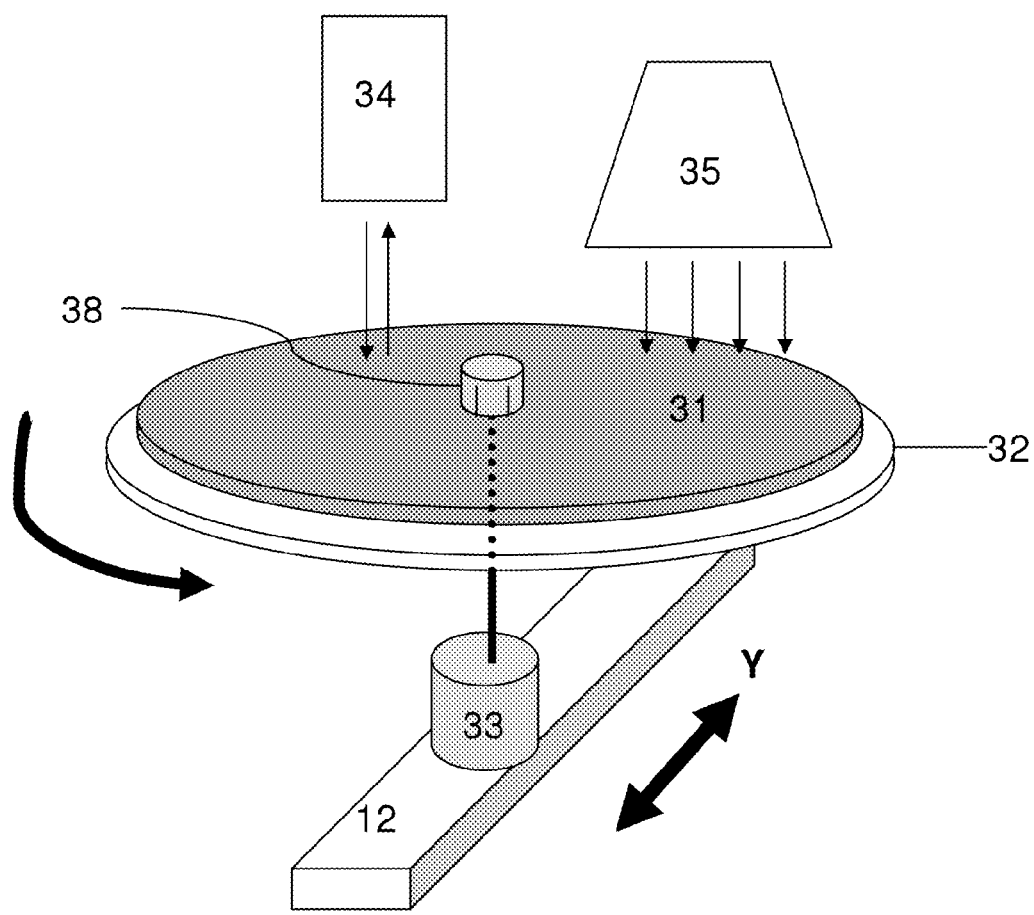
FIG. 7 is a schematic representation of an embodiment with a rotational scan mode.

Additional embodiments are illustrated in FIGS. 5, 6, and 7.

FIG. 5 is a simplified schematic representation of an embodiment using Laser-Induced-Breakdown Spectrometer (LIBS), in which the mechanisms of the fluid pan 8 and the X-Y table are omitted. In replacing the sparker 6 and the upper electrode 2, a probe 19 of LIBS is mounted in a direction perpendicular to the X-Y plane and above a flat sample plate 1. The probe 19 has a fixed coordinate in the X-Y plane while the plate 1 is movable in x and y direction by the X-Y table (not shown). The probe 19 delivers laser excitation energy to the plate 1 and also collects the light emitted from excitation spot, as depicted by a bi-directional arrow line. The fiber optical cable 17 is used to transfer the emitted light collected by the probe 19 to the spectrometer 5. The laser is powered by a power supply 22 which is commanded by the computer 16.

The plate 1 does not function as an electrode, but still function as an XY movable platform for a sample to receive the excitation energy in sequence. Because the excitation energy is delivered in the form of a laser beam to the surface of the plate 1, the excitation area on it is highly localized and only the sample at a small spot of the surface is excited at a time. The XY motion of the plate 1 provides the excitation to cover every point of a defined area of the surface.

Because a spot of laser beam is smaller than that of spark, a smaller excitation area on the surface is expected, which results in an improved spatial resolution.

In my contemplation, the flat sample plate 1 can be made of carbon as for the first embodiment. However, other materials can be used as long as the materials do not contain the chemical elements to be analyzed.

FIG. 6 demonstrates a simplified schematic representation of an embodiment utilizing X-ray as excitation energy, in which the mechanisms of fluid pan 8 and the X-Y table are omitted. An X-ray source 20 provides the excitation energy. It is mounted above a sample holder 60. The sample holder 60 has an extended flat surface area. Likewise, the sample holder 60 now only functions as an XY movable platform for a sample to receive the excitation energy in sequence. Once the X-ray beam from the X-ray source 20 illuminates a point on the sample surface of the holder 60, the sample at that point is excited to emit light, called X-Ray Fluorescence (XRF), as represented by the up-arrow in FIG. 6. An X-ray spectrometer 21 is also mounted above the holder 60 with the view of an X-ray detector aiming at the point where excitation occurs. Both of the X-ray source 20 and the spectrometer 21 are not movable in the X-Y plane. So the XY motion of the holder 60 provides the excitation to cover every point on the sample surface.

The sample holder 60 shall be made with non-backscattering material such as plastic, aluminum, carbon, and so on. If sample thickness is required for XRF sensitivity, the sample holder 60 may be shaped to a cup-like holder, as long as large wear metal particles can be retained and settled down in it. In this case, the fluid pan 8 still serves as an overflow reservoir. Thus operators do not need to take extra care for sample preparation.

For both embodiments depicted by FIG. 5 and FIG. 6, a heater-thermistor assembly 18 under or close to the flat plate 1 or the holder 60 provides heating to the sample if required. The computer 16 executes operation as described before.

Another embodiment comprises a rotational table 32, as shown in FIG. 7, in which the linear motion in X dimension is changed to rotation. Correspondingly, its sample plate 31 is a flat round plate, or a disk 31, and has an extended flat surface area. Sample is spread on the surface of the disk 31. The disk 31 is placed on the table 32, and can be optionally held by a mechanism 38, such as a screw. The table 32 is axially linked to a motor 33, which provides spin motion for the table 32 and so forth for the disk 31. The motor 33 is mounted on the carriage (not shown) moving on the Y guide way 12 and thus the table 32 and the disk 31 can move in Y direction. An excitation source 34 is mounted above the disk 31. The excitation source 34 may be the upper electrode 2 if spark is used, the LIBS probe 19 if laser is used or the X-ray source 20 and spectrometer 21 if XRF is used.

A microwave source 35 is mounted above the disk 31 and creates heat energy in a defined area, including the excitation point, of the sample spread on the disk 31.

A scan may be executed by coordinating the spin of the disk 31 with its motion in Y direction. The motion in Y direction may start by aligning the excitation source 34 either to an inner circle of the disk 31 and then goes outward, or in reverse. Once the rotation of the disk 31 finishes one cycle, it is moved on the Y guide way 12, either inward or outward, by a predetermined step and then spins for another cycle. The coordinated motion repeats until every point on the disk 31 is scanned. Likewise, emission spectrum is acquired at each point.

The spin direction of the disk 31 shall make the excitation point at the downstream of the heating area so that cooling of the sample at the excitation point is insignificant.

According to the embodiments disclosed above, a number of advantages of the provided method become evident:

For the aspect of introducing sample to an excitation site, there is no limitation to particle sizes so that large wear metal particles in the sample will be captured and identified by a simple immediate step, without the need for conducting any sample pretreatment.

For conventional spark method, the lower electrode is configured as a sample carrier and has relative motion against the upper electrode, which eliminates the requirement of a continuous flow of sample for a spark apparatus. Consequently, non-flowable samples will be able to enter a spark gap for excitation. Furthermore, because there is no restriction to the forms of sample to be presented to the spark gap, a single spark apparatus will be used to analyze plural forms of samples important to wear metal analysis, such as grease, coolant, vessel fuel, and so on.

For obtaining the information of inhomogeneous ingredients of a sample, such as the information of large particles in used oil, a method is provided by simply converting the inhomogeneity into to an uneven spatial distribution of elements on an extended surface. The inhomogeneity, in turn, will be spatially registered and evaluated by the emission spectra taken from the surface. And the provided method can be used for all kinds of atomic excitation approaches for emission spectroscopy, including, without limitation, spark, X-ray, and laser-induced-breakdown.

For applying heat energy to a sample for emission spectra, the extended surface area of the sample plate will increase the heat flux and produce improved heating effect. In addition, a method of heating-on-excitation will be provided to all kinds of atomic excitation approaches for emission spectroscopy, including, but not limited to, spark, X-ray, and laser-induced-breakdown.

The apparatus described by the above embodiments has additional advantages in that:

It provides an on-site analytical method for grease and coolant samples, which is not possible in prior art.

Because of the simplicity of operation, it permits wear metal analysis to be executed by non-skilled workers.

Further, the present invention is not restricted by all embodiments disclosed above. For example, the scanning apparatus may also scan by moving excitation source and optics while keeping the sample holder fixed. And the sample holder may be modified to various shapes. Scan pattern, spatial resolution, and scan velocity may also be modified. And other means of applying heat energy to an excitation site may also be used. It is to be understood that the invention is not limited to the particular forms disclosed. The invention covers all modifications, equivalents, alternatives falling within the spirit and scope of the invention as defined by the claims.

I claim:

1. An apparatus of emission spectroscopy for analyzing a deformable sample comprising:
    (a) a lower electrode which is flat and has an extended surface area for holding a sample to be excited thereon;
    (b) an upper rod electrode which has a predetermined tip pointing to but spaced apart the flat surface of said lower electrode;
    (c) a spark gap defined by the distance between the tip of said upper electrode and a position beneath on the flat surface of said lower electrode, whereby an induced spark ball will be localized at a predefined small area on the flat surface of said lower electrode;

(d) a spectrometer assembly with a predetermined integration time configured to aim at said spark gap for collecting and registering an emission with at least one wavelength generated solely from said position;

(e) means for providing horizontal motion to one of said electrodes along at least one dimension, at a predetermined speed, and following a predefined scan route in order for the spark ball to scan over the flat surface area on said lower electrode and for said spectrometer assembly to collect a plurality of emissions generated on said scan route;

(f) means for correlating said plurality of emissions to the scanned positions on said scan route and for individually evaluating an emission contribution from each of said scanned positions.

2. Apparatus of claim 1 wherein said spark gap having at least one horizontally movable electrode moving at least in one dimension.

3. The spark gap of claim 2 having an electrode heat-bathed by an energy source other than the excitation energy for generating atomic emission of a sample.

4. Apparatus of claim 1 wherein said lower electrode is composed of carbon.

5. Apparatus of claim 1 further comprising a heater for providing heat energy through a thermal conducting bed having a predefined sectional area to said lower electrode thereabove, whereby the sample on the entire surface of said lower electrode can be heated before and during sparking.

6. Apparatus of claim 1 further comprising means for sandwiching said heater between said lower electrode and a fluid pan.

7. The spark gap of claim 1 comprising a rod electrode and a flat electrode, said flat electrode having an extended surface area, and said rod electrode and said flat electrode are slidable over each other at least in one dimension, wherein the surface area of said flat electrode will be scanned by a spark plasma.

8. A method for analyzing plural elements of lubricant sample using emission spectroscopy comprising:

(a) using a flat plate having extended surface area for holding a sample and for receiving excitation energy which distorts the atomic structure of the elements thereon;

(b) using a point source delivering said excitation energy to a predefined position having a predetermined small area on said surface area;

(c) using observation means configured with a predetermined acquisition time for collecting and registering an emission with at least one wavelength generated solely from the sample at said position;

(d) using motion means for sliding at least either said flat plate or said observation means or said source or a block comprising both said observation means and said source along at least one dimension, at a predetermined speed, and with a predefined scan route in order for said source to scan over the sample on said plate and for said observation means to record a plurality of emissions generated on said scan route;

(e) using means for correlating said plurality of emissions to the scanned positions on said scan route and for individually evaluating an emission contribution from each of said scanned positions;

whereby the concentration of inhomogeneous ingredients of said sample will be individually evaluated.

9. A method of claim 8 further comprising:

employing means for delivering heat energy to said sample on said surface area through a predefined sectional area before or during the excitation of said sample, whereby the sample on the entire surface of surface area can be heated before and during atomic excitation is applied to said sample.

* * * * *